United States Patent [19]

Hardy et al.

[11] Patent Number: 4,458,035

[45] Date of Patent: Jul. 3, 1984

[54] POLYURETHANE FOAM HAVING A FLAME RETARDANT OLIGOMERIC PHOSPHATE ESTER

[75] Inventors: Thomas A. Hardy, Monroe; Fred Jaffe, Ossinging, both of N.Y.

[73] Assignee: Stauffer Chemical Company, Westport, Conn.

[21] Appl. No.: 440,788

[22] Filed: Nov. 12, 1982

Related U.S. Application Data

[62] Division of Ser. No. 318,288, Nov. 4, 1981, Pat. No. 4,382,042.

[51] Int. Cl.$^3$ .............................................. C08G 18/14
[52] U.S. Cl. ...................................... 521/107; 521/169
[58] Field of Search ................................ 521/107, 169

[56] References Cited

U.S. PATENT DOCUMENTS 3,767,732 10/1973 Klose .................................. 260/928

FOREIGN PATENT DOCUMENTS 942616 11/1963 United Kingdom .

*Primary Examiner*—Maurice J. Welsh
*Attorney, Agent, or Firm*—Roger S. Benjamin

[57] ABSTRACT

Flame retardant oligomeric phosphate ester compositions having the structural formula:

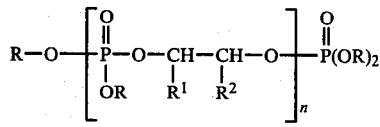

are prepared, wherein R is $C_1$-$C_{10}$ alkyl or haloalkyl, $R^1$ and $R^2$ can be the same or different and are hydrogen, $C_1$-$C_{10}$ alkyl or haloalkyl and n is an integer from zero to about 10.

The method of preparing the compositions comprises reacting $P_2O_5$ with a trialkyl or tris(haloalkyl)phosphate in the presence of about 0.01% to about 5% of a phosphite at a temperature from about 0°–200° C. A polyphosphate ester having P—O—P bonds is formed which is then reacted with an epoxide to yield the oligomeric phosphate ester flame retardant compositions.

Alternatively, a method of preparing similar compositions comprises reacting $P_2O_5$ with a trialkyl or tris (haloalkyl)phosphite at a temperature from about 0° C. to about 200° C. A mixed polyphosphate-polyphosphite ester having P—O—P bonds is formed which is then oxidized to yield a polyphosphate having P—O—P bonds; which is then reacted with an epoxide to yield the oligomeric phosphate ester flame retardant compositions.

3 Claims, No Drawings

POLYURETHANE FOAM HAVING A FLAME RETARDANT OLIGOMERIC PHOSPHATE ESTER

This is a division of application Ser. No. 318,288 filed Nov. 4, 1981, now U.S. Pat. No. 4,382,042.

BACKGROUND OF THE INVENTION

1. Field of the Invention

The present invention relates, in general, to flame retardant oligomers, and particularly concerns a method of preparing flame retardant oligomeric phosphate esters.

2. The Prior Art

Oligomeric phosphate esters are known and are described in U.S. Pat. No. 3,767,732. U.S. Pat. No. 3,767,732 patent discloses compositions having the structural formula:

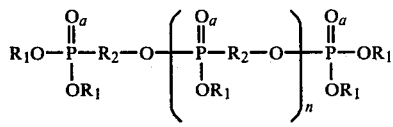

wherein a stands for 1 or 0, n stands for a number between 0 and 4, $R_1$ stands for at least one halogenated hydrocarbon radical and at least one hydroxylated radical of the structural formula:

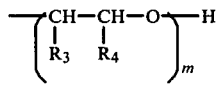

and $R_2$ stands for a radical of the structural formula:

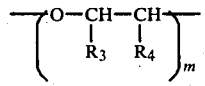

The substituents $R_3$ and $R_4$ respectively stand for a hydrogen atom or a hydrocarbon radical having from 1 to 6 carbon atoms and being halogen substitued, if desired, and m stands for a number between 1 and 10.

The method of preparing the compositions of U.S. Pat. No. 3,767,732 comprises reacting a compound of the structural formula:

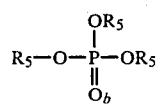

wherein $R_5$ is chloroethyl or 2,3-dibromopropyl and b is 0 or 1; in the presence of between about 0.1 and 2 percent of a phosphorus acid stabilizer and between about 0.1 and 2 percent of disodium phosphate with a polyphosphoric acid or a mixture thereof with $P_2O_5$. A reaction mixture of partially esterified polyphosphoric acids is prepared by this step. The reaction mixture is then further reacted with an epoxide having the structural formula:

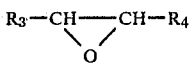

wherein $R_3$ and $R_4$ are as defined above; until said partially esterified polyphosphoric acids are completely esterified. The product is a reactive flame retardant having hydroxyl numbers from about 100 to 300 milligrams of KOH per gram of product.

It is known that reactive flame retardants are undesirable for flexible polyurethane foams. They are detrimental to the flexibility of the foams and can cause other undesirable side effects to the foam properties.

SUMMARY OF THE INVENTION

In accordance with the present invention, flame retardant oligomeric phosphate esters having hydroxyl numbers from 1 to about 25 milligrams of KOH per gram of product are prepared. These oligomers have excellent flame retardancy characteristics as additive flame retardants for flexible polyurethane foams. Their additive nature prevents damage to the physical characteristics of flexible polyurethane foams. Furthermore, their oligomeric nature substantially reduces leaching of the flame retardant from the foam; thereby obviating a common undesirable characteristic of non-oligomeric additive flame retardants.

The method of the present invention comprises first reacting $P_2O_5$ with a trialkyl or tris(haloalkyl)phosphate in the presence of about 0.01% to about 5% of a phosphite at a temperature from about 0° C. to about 200° C. The reaction product is a mixed polyphosphate ester containing P—O—P bonds which is then reacted with an epoxide.

Alternatively, $P_2O_5$ is first reacted with a trialkyl or tris(haloalkyl)phosphite at a temperature from about 0° C. to about 200° C. The reaction product is a mixed polyphosphate-polyphosphite ester containing P—O—P bonds; which is oxidized with air or oxygen to yield a polyphosphate ester having P—O—P bonds; which is then reacted with an epoxide. A Lewis acid catalyst or an alcohol or both are employed during the epoxide reaction to insure complete reaction of latent acidity groups. Volatile materials are removed following the epoxide reaction.

DETAILED DESCRIPTION OF THE INVENTION

The oligomeric phosphate ester compositions of the present invention have the structural formula:

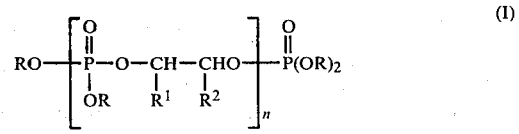

wherein R is $C_1$–$C_{10}$ alkyl or haloalkyl, $R^1$ and $R^2$ can be the same or different and are hydrogen or $C_1$–$C_{10}$ alkyl or haloalkyl and n is an integer from zero to about 10.

Exemplary R groups include but are not limited to the following:

| | |
|---|---|
| —$CH_3$ | —$CH_2CHBrCH_2Br$ |
| —$C_2H_5$ | —$CH_2CHClCH_2Cl$ |

-continued

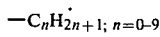

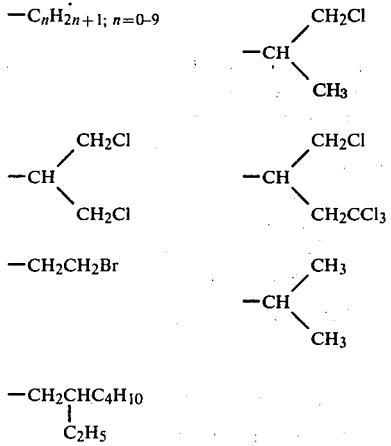

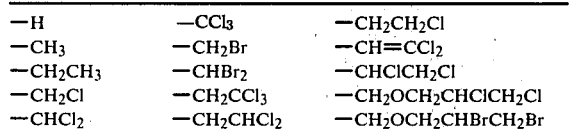

Exemplary $R^1$ and $R^2$ groups include but are not limited to the following:

| | | |
|---|---|---|
| —H | —CCl₃ | —CH₂CH₂Cl |
| —CH₃ | —CH₂Br | —CH=CCl₂ |
| —CH₂CH₃ | —CHBr₂ | —CHClCH₂Cl |
| —CH₂Cl | —CH₂CCl₃ | —CH₂OCH₂CHClCH₂Cl |
| —CHCl₂ | —CH₂CHCl₂ | —CH₂OCH₂CHBrCH₂Br |

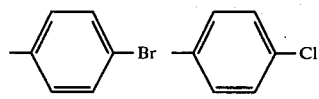

The method of preparing the oligomeric phosphate esters of the present invention comprises first reacting P₂O₅ with a trialkyl or tris(haloalkyl)phosphate having the structural formula:

   (II)

wherein R is the same as defined above.

This reaction is conducted at a temperature from about 0° C. to about 200° C. in the presence of about 0.01% to about 5% of a phosphite having the structural formula:

P(OR)₃   (III)

wherein R is the same as defined above.

Alternatively, P₂O₅ can be reacted with a trialkyl phoshite having the structural formula (III) at a temperature from about 0° C. to about 200° C. The product is then a mixed polyphosphate-polyphosphite ester having P—O—P bonds which is oxidized by reacting with air or oxygen at a temperature from about 0° C. to about 200° C.

The reaction product is a polyphosphate ester having P—O—P bonds which is then reacted at a temperature from about 0° C. to about 200° C. with an excess of an epoxide having the structural formula:

   (IV)

wherein $R^1$ and $R^2$ are the same as defined above. The excess epoxide insures complete reaction of all P—O—P bonds. This step can be carried out at elevated pressure to prevent loss of a volatile epoxide.

A Lewis acid catalyst or an alcohol or both are employed in amounts from about 0.01% to about 5% during the epoxide reaction to insure complete reaction of latent acidity groups.

Suitable Lewis acid catalysts include but are not limited to the following:

| | |
|---|---|
| Aluminum Chloride | Boron Trifluoride Etherate |
| Tetra(Isopropyl)Titanate | Boron Trifluoride |
| Stannous Octoate | Zinc Chloride |
| Magnesium Chloride | Antimony Trichloride |
| Titanium Tetrachloride | |

Suitable alcohols include but are not limited to the following:

| | |
|---|---|
| CH₃OH | CH₃(CH₂)ₙOH; n = 2–10 |
| C₂H₅OH | (BrCH₂)₃CCH₂OH |
| CH₃\\<br>  CHOH<br>CH₃/ | φCH₂OH |

Following the epoxide reaction, volatile materials are removed from the reaction product. This can be accomplished by vacuum stripping, nitrogen sparging, CO₂ sparging, dry air sparging, or combined vacuum and inert gas sparging.

The following equations (1) and (2) are representative of the reaction:

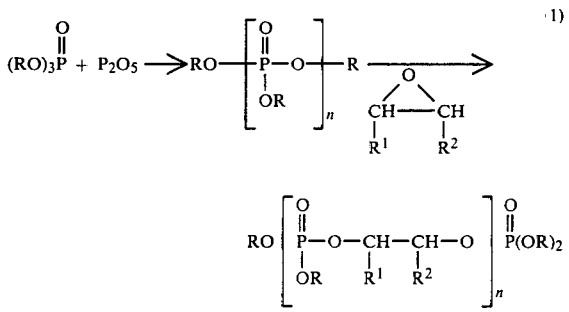   (1)

wherein R, $R^1$, $R^2$ and n are the same as defined above, or alternatively:

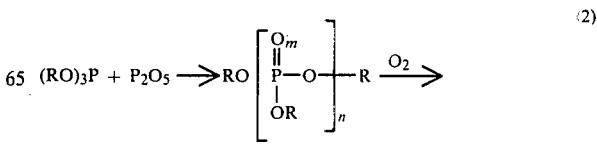   (2)

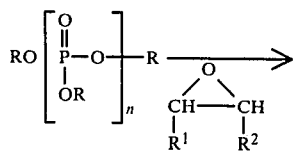

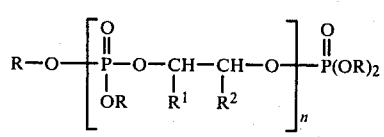

where R, R¹, R² and n are as defined above and m is 0 or 1.

Reactants utilized in the method described above are generally employed in suitable ratios to give a product with the desired %P, %Cl, viscosity, and oligomeric composition. The ratio of $P_2O_5$ to trialkyl phosphate or tris(haloalkyl)phosphate, or alternately the ratio of $P_2O_5$ to trialkyl or tris(haloalkyl)phosphite, can be varied over a wide range. A variety of compositions can be prepared by altering the stoichiometry of reagents.

Reaction times can vary over relatively wide ranges and can easily be determined by one skilled in the art. Factors affecting reaction time include reactant and catalyst concentrations and temperature. Increases in temperature and catalyst concentration result in decreased reaction times. Typical reaction times are from about 1 to about 30 hours for each step.

The method described above can conveniently be effected by introducing the individual reactants and catalyst into any reaction zone that can be heated to the reaction temperature. The zone is generally provided with a condenser for removal of volatile components. A thermometer, thermocouple or other conventional means can be used to monitor temperature. The reaction can be carried out in a continuous or batch-type system as desired.

The products of the reaction are generally purified by removal of volatiles. This can be accomplished by conventional techniques.

The identification of products can be achieved by infrared spectra, ¹H nuclear magnetic resonance spectra and ³¹P nuclear magnetic resonance spectra and elemental analysis.

Typical yields of the above-described method of the present invention are about 100% based on $P_2O_5$.

The hydroxyl number of the products is generally from about 1 to about 25 milligrams of KOH per gram of product. Accordingly, the products are essentially non-reactive in flexible polyurethane foams.

Illustrative of the compounds corresponding to structural formula (I) which can be prepared by the method of the present invention are:

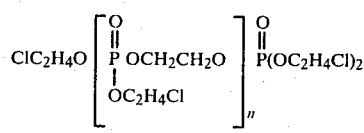

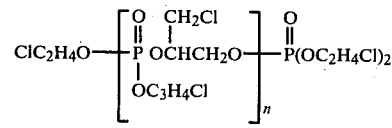

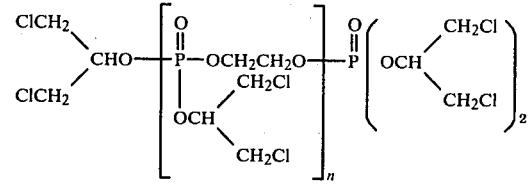

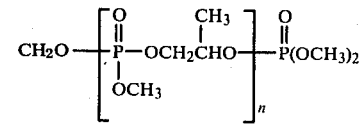

Where n is as defined above. Branched oligomers of the foregoing idealized structures may be also be present.

The products of the present invention are useful for various flame retardant applications. They are particularly suited, however, for flame retarding flexible polyurethane foams.

The present invention will be more fully illustrated in the Examples which follow:

EXAMPLE 1

A reactor equipped with an agitator, thermometer, gas inlet and reflux condenser was charged with 1000 g of tris(2-chloroethyl)phosphate and 10 g of tris(2-chloroethyl)phosphite. The solution was warmed to 50° C. and 200 g of phosphorus pentoxide was added, with the exclusion of moisture and air. The slurry was then heated to 110°–120° C. until the phosphorus pentoxide dissolved. Two grams of isopropyl alcohol was added, and ethylene oxided was introduced to the mixture at 110°–120° C. until reaction ceased. This was indicated by strong reflux of ethylene oxide on a dry ice condenser. Two more grams of isopropyl alcohol and two grams of stannous octoate were added and ethylene oxide was introduced to the solution at 110°–120° C. until the reaction ceased. The product was then stripped at 50° C. and 5 mm of Hg, yielding 1457 g of a water white liquid with a viscosity of 1100 cps (at 25° C.) and an acid number of 0.8 mg KOH/g. The product had a hydroxyl number of 12 mg KOH/g, and was found to contain 14.0% phosphorus and 24.5% chlorine.

EXAMPLE 2

A reactor equipped with an agitator, thermometer, gas inlet and reflux condenser was charged with 1000 g of tris(2-chloroethyl)phosphate and 10 g of tris(2-chloroethyl)phosphite.

After 27 minutes of heating with the temperature at 50° C., 250 g of phosphorus pentoxide was added, with the exclusion of moisture and air.

The slurry was then heated to 115°–120° C. for 10 hours until the phosphorus pentoxide was dissolved. Ethylene oxide was then introduced to the mixture at 110°–120° C. until reaction ceased. This was indicated by a strong reflux of ethylene oxide on the side of the condenser. Two grams of stannous octoate was added and ethylene oxide was introduced to the solution at 110°–120° C. until reaction ceased.

Another 2 g of stannous octoate and 2 g of isopropanol were then added and ethylene oxide was again introduced until reaction ceased. The total time used for ethylene oxide addition was 17½ hours.

The product was then stripped at 60° C. and 2 mm of Hg for 90 minutes.

1500 g of a water white liquid with a viscosity of 2600 cps (at 25° C.) and an acid number of 0.8 mg KOH/g was obtained. The product had a hydroxyl number of 13.5 mg KOH/g.

EXAMPLE 3

A reactor equipped with an agitator, thermometer, gas inlet and reflux condenser was charged with 1250 g of tris(dichloropropyl)phosphite. The solution was warmed to 130° C. and 110 g of $P_2O_5$ was added. After 1 hour the $P_2O_5$ had dissolved and oxygen gas was bubbled through the solution at 125°–135° C. over 3 hours. At this point 5 g of isopropyl alcohol was added, and ethylene oxide was introduced. After 4 hours, 2 g of stannous octoate was added and addition of ethylene oxide was resumed. After 4 more hours, 2 g of stannous octoate was again added, and the ethylene oxide reaction continued for another 2 hours. The product was cooled to 80° C. and stripped at 1 mm of Hg.

1450 g of a light yellow material with a viscosity of 34,000 cps (at 25° C.) and an acid number of 1.4 mg KOH/g was obtained. The product was found to have a hydroxyl number of 8 mg KOH/g, and to contain 9.2% phosphorus and 37.5% chlorine.

EXAMPLE 4

A reactor was charged with 600 pounds of tris(2-chloroethyl)phosphate and 6 lbs of tris 2(chloroethyl) phosphite. The mixture was then heated over 75 minutes to 43° C.; and 120 lbs of phosphorus pentoxide was added. The slurry was heated at 108° C. for 10 hrs. The batch was then cooled to 92° C. over 1 hour; then 2 lbs of tris(2-chloroethyl)phosphite was added. Over a 26 hour period a total of 162.5 lbs of ethylene oxide was added to the solution at 95°–105° C. with addition of 2.4 lbs of stannous octoate and 4.8 lbs of isopropyl alcohol to facilitate the reaction. The batch was then cooled to 45° C. and volatiles were removed at 5 mm of Hg for 2 hours. A total of 839 pounds of almost water white product with a viscosity of 1030 cps, an acid number of 0.8 mg KOH/g and a hydroxyl number 10.5 mg KOH/g was obtained. The product was found to contain 13.8% phosphorus and 26.7% chlorine.

EXAMPLE 5

A reactor equipped with an agitator, thermometer, gas inlet and reflux condenser was charged with 1300 g of tris(dichloropropyl)phosphate and 5 g of tris(2-chloroethyl)phosphite. With the temperature at 25° C., 175 g of phosphorus pentoxide was added with the exclusion of moisture and air.

The slurry was then heated for 4 hours at 80° C. A brown discoloration appeared and 5 grams more of tris(2-chloroethyl)phosphite was added to the system. The system was then heated for an additional 2½ hours at 100°–110° C. until the phosphorus pentoxide dissolved.

Two grams of isopropyl alcohol was added and ethylene oxide was introduced to the mixture at 110°–120° C. until reaction ceased. This was indicated by a strong reflux of ethylene oxide on a dry ice condenser. Two more grams of isopropanol and 2 g of stannous octoate were added and ethylene oxide was introduced to the solution at 110°–120° C. until the reaction ceased.

The product was then stripped at 40° C. and 4 mm of Hg, yielding 1645 g of a pale orange liquid with a viscosity of 28,000 cps (at 25° C.) and an acid number of 0.8 mg KOH/g. The product has a hydroxyl number of 17.2 mg KOH/g and was found to contain 10.1% phosphorus and 37% chlorine.

EXAMPLE 4

A reactor equipped with an agitator, thermometer, gas inlet and reflux condenser was charged with 800 g of tris(2-chloroethyl)phosphate, 400 g of tris(dichloropropyl) phosphate and 10 g of tris(2-chloroethyl)phosphite. With the temperature at 27° C., 80 g of phosphorus pentoxide was added with the exclusion of air and moisture.

The slurry was then heated for 2½ hours. Ethylene oxide was introduced to the mixture at 110°–120° C. until reaction ceased. This was indicated by a strong reflux of ethylene oxide in the condenser.

Two grams of isopropyl alcohol and 2 g of stannous octoate were added and ethylene oxide was introduced to the mixture at 110°–120° C. until the reaction ceased.

Two more grams of stannous octoate and 2 g of isopropanol were then added and ethylene oxide was introduced to the solution at 110°–120° C. until the reaction ceased.

The product was then stripped at 40° C. and 1 mm Hg, yielding 1340 g of a water white product with a viscosity of 1050 cps (at 25° C.) an acid number of 0.84 mg KOH/g and an hydroxyl number of 9.5 mg KOH/g. The product was found to contain 10.6% phosphorus and 35.8% chlorine.

EXAMPLE 7

A reactor equipped with an agitator, thermometer, gas inlet and reflux condenser was charged with 550 g of tris(dichloropropyl)phosphate, 800 g of tris(2-chloroethyl)phosphate and 10 g of tris(2-chloroethyl)phosphite. With the temperature at 25° C., 160 g of phosphorus pentoxide was added with the exclusion of moisture and air.

The slurry was then heated at 115°–120° C. for 6 hours until the phosphorus pentoxide had dissolved. Two grams of isopropyl alcohol was added and ethylene oxide was introduced to the mixture at 110°–120° C. until reaction ceased. This was indicated by a strong reflux of ethylene oxide in a dry ice condenser.

Two more grams of isopropanol and 2 g of stannous octoate were added and ethylene oxide was introduced to the solution at 110°–120° C. until the reaction ceased.

Another 2 g of stannous octoate was added and ethylene oxide was introduced to the solution at 110°–120° C. until the reaction ceased.

The product was then stripped at 50° C. and 2 mm/Hg, yielding 1666 g of an almost water white product with a viscosity of 1050 cps (at 25° C.) and an acid number of 1.12 mg KOH/g and an hydroxyl number of 95 mg KOH/g. The product was found to contain 11.6% phosphorus and 32.9% chlorine.

EXAMPLE 8

The composition prepared pursuant to Example 5 was incorporated at 9 p.h.r. into a flexible polyurethane foam having the following formulation:

| | Parts by Weight |
|---|---|
| oxypropylated glycerin | 100.0 |
| silicone surfactant | 1.0 |
| triethylenediamine catalyst | 0.1 |
| N—ethyl morphiline | 0.2 |
| water | 4.0 |
| stannous octoate catalyst | 0.2 |
| tolylene diisocyanate | 50.67 |

The foam mixture was poured into an open-top box and allowed to expand into a 15 inch square block. It was then oven cured at 130° C. for about 10 minutes. This was followed by ambient temperature curing for 3 days.

Flammability testing was conducted pursuant to the California Vertical burn test and Motor Vehicle Safety Standard 302 (MVSS-302). A control foam of the same formulation without the flame retardant was also prepared and tested for flammability.

Particulars on the California Vertical burn test are available from the State of California in Technical Information Bulletin 117. In the MVSS-302 test, a specimen of foam $4'' \times \frac{1}{2}''$ thick by 14" long is held horizontally between two U-shaped brackets which allow free access of air above and below. The specimen is ignited by a bunsen burner and the burning rate in inches per minute is measured. A burn rate below 4"/min. is usually required.

General Motors Corporation uses the following qualitative measures under MVSS-302:

| Does not ignite | DNI |
|---|---|
| Self extinguishes (SE) before first mark (before 1½" total) | SE |
| SE in less than 3½" total | SE/NBR |
| SE after 3½" from starting point | SE, a burn rate |
| Burns full length | burn rate |

The flammability results were as follows:

| | CONTROL | FLAME RETARDED FOAM |
|---|---|---|
| MVSS-302 | | |
| INITIAL RATING | BURN | SE/NBR |
| Avg In Burned | 11.50 | 1.46 |
| Avg Sec Burned | 130.00 | 0.50 |
| Burn Rate | 4.63 | |
| DHA* RATING | BURN | SE/NBR |
| Avg In Burned | 9.90 | 1.15 |
| Avg Sec Burned | 107.89 | |
| Burn Rate | 4.92 | |
| CALIF. VERTICAL | | |
| INITIAL RATING | FAIL | PASS |
| Avg In Burned | 12.00 | 2.45 |
| Avg Sec Burned | 9.20 | |
| DHA*RATING | FAIL | PASS |
| Avg. In Burned | 12.00 | 2.75 |
| Avg Sec Burned | 9.60 | |

*Dry heat aging for 22 hours at 140° C.

EXAMPLE 9

The composition prepared pursuant to Example 6 was incorporated at 10 p.h.r. into a flexible polyurethane foam having the same formulation and physical characteristics as that described in Example 8. The control foam of Example 8 was used as a reference.

Flammability testing results were as follows:

| | CONTROL | FLAME RETARDED FOAM |
|---|---|---|
| MVSS-302 | | |
| INITIAL RATING | BURN | SE/NBR |
| Avg In Burned | 11.50 | 1.19 |
| Avg Sec Burned | 130.00 | |
| Burn Rate | 4.63 | |
| DHA RATING | BURN | SE/NBR |
| Avg In Burned | 9.90 | 1.32 |
| Avg Sec Burned | 107.80 | 0.20 |
| Burn Rate | 4.92 | |
| CALIF. VERTICAL | | |
| INITIAL RATING | FAIL | PASS |
| Avg In Burned | 12.00 | 2.15 |
| Avg Sec Burned | 9.20 | |
| DHA RATING | FAIL | PASS |
| Avg In Burned | 12.00 | 2.55 |
| Avg Sec Burned | 9.60 | |

Having set forth the general nature and some examples of the present invention, the scope is now specifically set forth in the appended claims.

What is claimed is:

1. A flexible polyurethane foam having a flame retardant effective amount of an oligomeric phosphate ester composition of the structural formula:

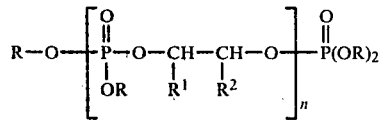

wherein R is $C_1$–$C_{10}$ alkyl or $C_1$–$C_{10}$ haloalkyl; $R^1$ and $R^2$ are the same or different and are hydrogen, $C_1$–$C_{10}$ alkyl or $C_1$–$C_{10}$ haloalkyl and n is an integer from 2 to about 10; said oligomeric phosphate ester composition having been prepared by first reacting $P_2O_5$ with a trialkyl or tris(haloalkyl)phosphate of the structural formula:

wherein R is the same as defined above, at a temperature from about 0° C. to about 200° C. in the presence of about 0.01% to about 5% of a phosphite of the structural formula:

wherein R is as defined above; followed by reacting the intermediate produced by the first reaction with an excess of an epoxide of the structural formula:

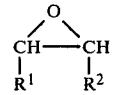

wherein $R^1$ and $R^2$ are as defined above, at a temperature from about 0° C. to about 200° C.

2. The composition of claim 1 wherein R is selected from the group consisting of methyl, ethyl, propyl, isopropyl, straight or branched butyl, chloroethyl, chloropropyl, chloroisopropyl, dichloroethyl, dichloroisopropyl, dichloropropyl, bromoethyl, bromopropyl, bromoisopropyl, dibromoethyl, dibromoisopropyl and dibromopropyl.

3. The composition of claim 1 wherein $R^1$ and $R^2$ are the same or different and are selected from the group consisting of hydrogen, methyl, ethyl, propyl, isopropyl, straight or branched butyl, chloromethyl, chloroethyl, chloropropyl, chloroisopropyl, dichloroethyl, dichloropropyl, dichloroisopropyl, bromoethyl, bromoethyl, bromopropyl, bromoisopropyl, dibromoethyl, dibromopropyl and dibromoisopropyl.

* * * * *

UNITED STATES PATENT AND TRADEMARK OFFICE
CERTIFICATE OF CORRECTION

PATENT NO. : 4,458,035
DATED : July 3, 1984
INVENTOR(S) : Thomas A. Hardy et al.

It is certified that error appears in the above—identified patent and that said Letters Patent is hereby corrected as shown below:

Col. 1, lines 17-18, "U.S. Patent No. 3,767,732" should be -- The '732 patent --;

Col. 3, line 6, the formula -- $-CH_2CH_2Cl$ -- should appear below "$-C_nH_{2n+1}$; n = 0-9";

Col. 6, lines 1-7, the formula should read:

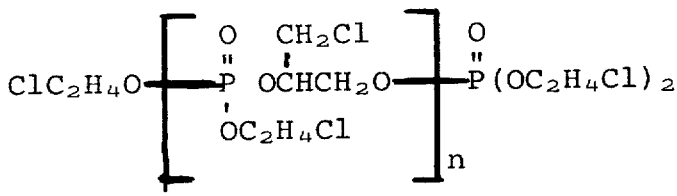

Col. 6, lines 17-22, the formula should read:

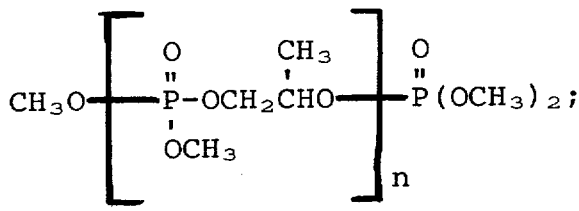

UNITED STATES PATENT AND TRADEMARK OFFICE
CERTIFICATE OF CORRECTION

PATENT NO. : 4,458,035

DATED : July 3, 1984

INVENTOR(S) : Thomas A. Hardy et al.

It is certified that error appears in the above—identified patent and that said Letters Patent is hereby corrected as shown below:

Col. 6, line 24, "may be also" should read -- may also --;
Col. 6, line 41, "oxided" should be -- oxide --;
Col. 8, line 12, "EXAMPLE 4" should read -- EXAMPLE 6 --; and
Col. 12, line 3, "bromoethyl," should be deleted.

Signed and Sealed this

Second Day of April 1985

[SEAL]

Attest:

DONALD J. QUIGG

Attesting Officer     Acting Commissioner of Patents and Trademarks